United States Patent [19]

Crockett et al.

[11] 4,243,531
[45] Jan. 6, 1981

[54] CARDIOTOMY RESERVOIR

[75] Inventors: Thomas W. Crockett, Burlington, Wis.; Patrick N. Huehls, Highland Park; Barry G. Slotnick, Des Plaines, both of Ill.

[73] Assignee: Baxter Travenol Laboratories, Inc., Deerfield, Ill.

[21] Appl. No.: 910,323

[22] Filed: May 30, 1978

[51] Int. Cl.³ ............................................. B01D 19/02
[52] U.S. Cl. ..................................... 210/188; 55/178; 55/202; 210/436; 210/442; 210/456; 210/489; 210/927
[58] Field of Search ...................... 210/321 B, 22, 456, 210/436, 188, 442, 484, DIG. 23; 23/258.5 M, 258.5 BH; 55/202, 178

[56] References Cited

U.S. PATENT DOCUMENTS

| | | | |
|---|---|---|---|
| 1,452,253 | 4/1923 | Nevitt | 55/202 |
| 2,952,330 | 9/1960 | Wihslow | 55/202 |
| 3,488,158 | 1/1970 | Bentley et al. | 23/258.5 BH |
| 3,768,653 | 10/1973 | Brumfield | 210/436 X |
| 3,795,088 | 3/1974 | Esmond | 210/436 X |
| 3,891,416 | 6/1975 | Leonard et al. | 55/178 |
| 3,993,461 | 11/1976 | Leonard et al. | 55/178 |
| 4,038,191 | 7/1977 | Davis et al. | 210/321 B |
| 4,067,696 | 1/1978 | Curtis | 23/258.5 BH X |

OTHER PUBLICATIONS

Bentley Lab, Inc. Circular PN101402 Rev. B-11-76-1179PG, 6 pp.

Primary Examiner—Frank A. Spear, Jr.
Attorney, Agent, or Firm—Paul C. Flattery; Garrettson Ellis

[57] ABSTRACT

A reservoir for blood or the like in which a rigid casing, having a perforated tubular member positioned within the casing and extending between the ends thereof, carries filtering and blood defoaming means. An improved configuration of inlet aperture means is provided. Also, the reservoir may define an upstanding central hump at its lower end, surrounded by an annular trough positioned at an acute angle to the axis of the perforated tubular member, for improved recovery of blood from the reservoir and improved calibration of the amount of blood in the reservoir.

7 Claims, 4 Drawing Figures

CARDIOTOMY RESERVOIR

BACKGROUND OF THE INVENTION

Cardiotomy reservoirs are currently used in major surgical procedures, such as open heart surgery, for receiving blood from a cardiotomy sucker and other sources, for defoaming the blood, filtering out debris and returning it to the patient.

Numerous designs of cardiotomy reservoirs are commercially offered, for example, a cardiotomy reservoir similar to that disclosed in U.S. Pat. No. 3,993,461, and its predecessor in design being as disclosed in U.S. Pat. No. 3,891,416. In both of these cardiotomy reservoirs, a hollow casing is provided in which a tubular member is positioned within the casing and extends between the ends thereof. Blood enters the bottom of the tubular member, rising upwardly until it passes out of an aperture to the exterior of the tubular member.

The Shiley cardiotomy reservoir which is currently commercially available also comprises a casing having a tubular member extending through the interior from end to end, with filter and defoaming material carried outside of the tubular member. Blood enters the top of the reservoir through inlet ports at a side thereof, then normally falling downwardly and then passing through the defoaming material within the casing from where it is returned to the patient. The space within the tubular member is not used.

The lower end of the tubular member of the Shiley reservoir is retained by a bottom hump, in the lower end of the casing. The periphery of the lower end is sloped slightly to allow blood to flow to the lowest point, where the outlet is positioned.

One problem with this reservoir and its side entry blood inlet ports is that some blood coming in one port can swing around the circumference of the tubular casing and flow out one of the other ports, rather than falling downwardly into the defoaming material.

In introducing blood to a cardiotomy reservoir, it is also highly desirable to avoid the harsh impingement of blood upon a wall surface or the like, since that can result in an increase in the hemolysis level of the blood. On the other hand, blood which is introduced into one of the entry ports of a cardiotomy reservoir should not have the tendency to squirt out of the other entry ports. Furthermore, the reservoir should have a configuration that prevents the trapping of air pockets during use. Likewise, it is desirable to be able to provide calibration of the amount of blood in the reservoir, down to volumes as low as 25 or 50 cc..

The above and other advantages are provided in the cardiotomy reservoir of this invention, for improved processing of blood with reduced hemolysis.

DESCRIPTION OF THE INVENTION

In accordance with this invention a blood reservoir is provided which comprises a rigid casing and a perforated tubular member positioned within the casing and extending between the ends thereof. Inlet aperture means are positioned at the upper end of the reservoir in communication with the bore of the tubular member, to provide fluide communication from the exterior to the bore.

Flow aperture means positioned at the lower end of the tubular member provide fluid communication between the bore and the casing interior. The bore preferably contains a blood defoaming means such as conventional, silicone-coated sponge or metal turnings as has been previously used in bubble-type oxygenators. Also, the tubular member carries blood clot filter means, typically on its exterior, to filter flow through the perforations of the tubular member and the flow aperture means.

The inlet aperture meand defines a plurality of tubular apertures having open ends which are outwardly directed normally of the longitudinal axis of the tubular member. These apertures terminate inwardly in open-bottom, downwardly curved end wall means, to direct fluid flow inwardly through the apertures and then downwardly by means of a gentle, curved flow into the defoaming means.

Outlet aperture means are positioned adjacent the bottom of the casing.

Preferably, side walls project downwardly from the downwardly curved end wall means, to prevent the interconnecting flow of blood or other fluid from one of the tubular apertures to another, to prevent the spurting of blood out of an open inlet aperture.

Also, it is preferred for the tubular apertures to be each positioned radially about the axis of the tubular member. Typically, the tubular apertures are all positioned in no more than an arc of 120°.

At the bottom of the casing, it is preferred for the reservoir to define an upstanding central hump surrounded by an annular trough. The plane of the bottom of the annular trough preferably defines an acute angle to the axis of the tubular member, preferably 45° to 70° with the outlet aperture communicating through the lowest portion of the trough. This causes the liquid level at low volumes to change substantially with small changes in liquid volume. Thus, small amounts of blood in the reservoir can be accurately measured down to 25 or 50 cc.. A perforated plate member may be carried on the hump, with the plate member carrying the lower end of the tubular member.

The cardiotomy reservoir of this invention operates without spilling blood out of the various upper apertures, as has been a possibility in certain prior embodiments, and also has improved foam-removing capacity because of the position of the defoaming material within the bore of the tubular member with respect to the inlet. The defoaming material also deflects the downward flow of the blood so that the cells do not impact with great velocity on any surface after a substantial fall, but instead they fall gently in a circuitous path through the bulk of the defoaming sponge and then out of the bottom or sides of the tubular member, through the filter means.

Referring to the drawings.

Figure 1:
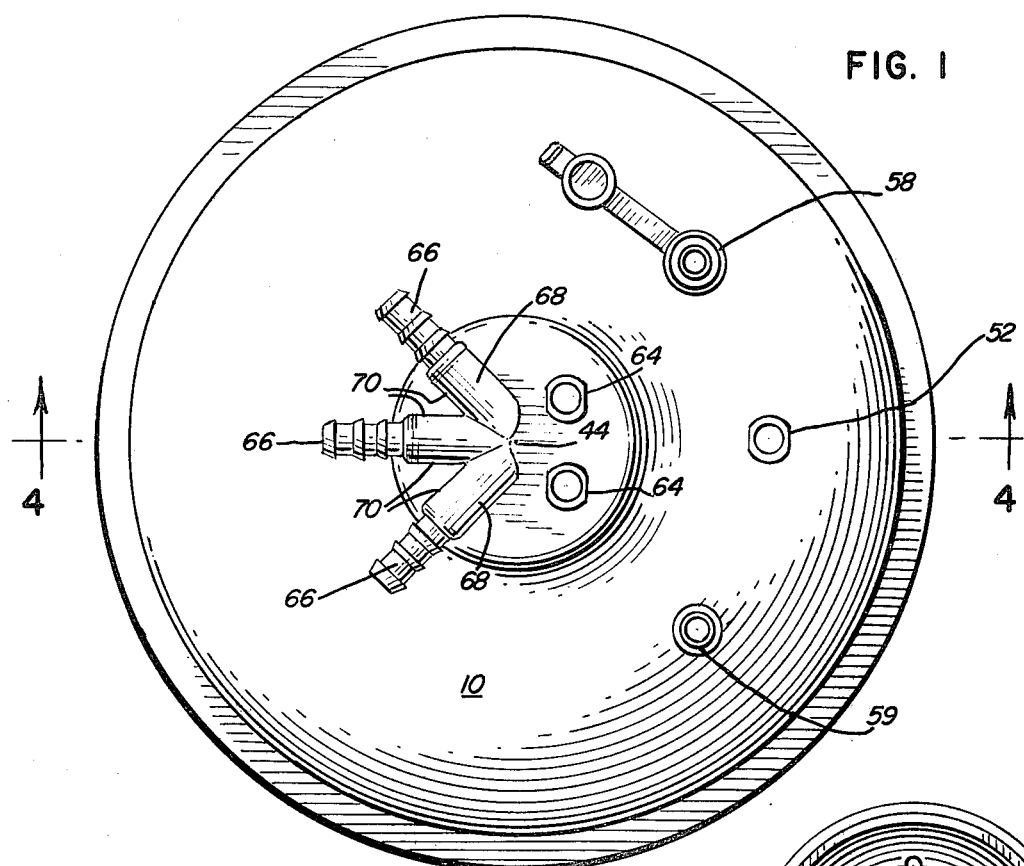
FIG. 1 is a top plan view of the cardiotomy reservoir of this invention.
Figure 4:
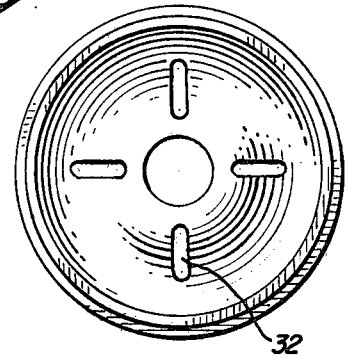
FIG. 4 is a plan view of the isolated perforated plate member which carries the lower end of the tubular member.

Referring to the drawings, cardiotomy reservoir 10 comprises a rigid housing 12, which may be made from a pair of shells 14, 16, sealed together about flanges 18 by radio frequency sealing, solvent sealing, or the like. Casing 12 may be made of transparent acrylic plastic or similar material.

Figure 3:
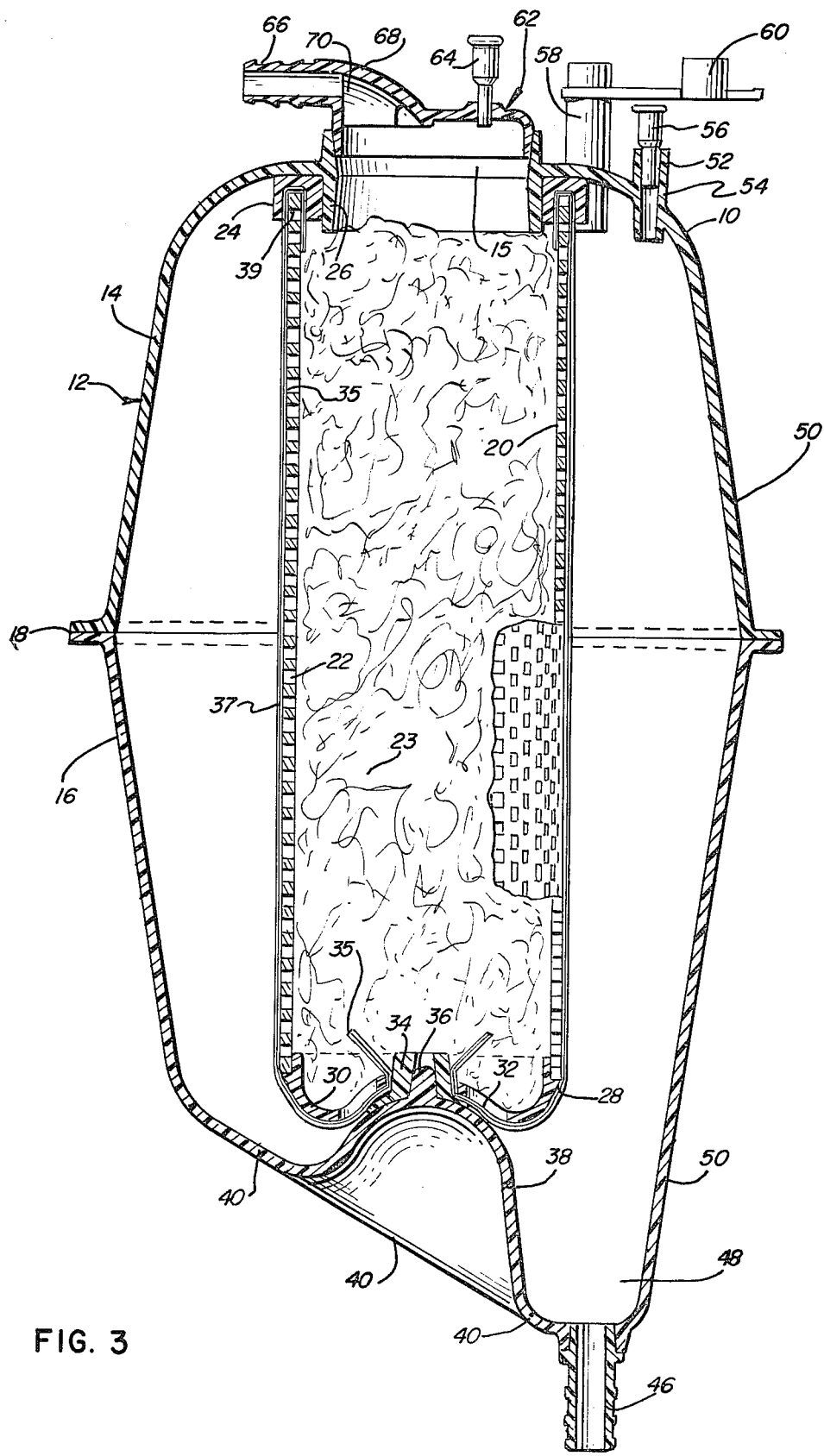
FIG. 3 is a sectional view taken along the line 3—3 of FIG. 1.

As shown in FIG. 3, casing 12 encloses a perforated tubular member 20, which may be made out of polyethylene, and typically carries numerous perforations 22 so that the walls of the tubular member can pass fluids. The upper end of tubular member 20 is positioned within an annular gasket 24 which may be made out of silicone rubber, and which fits about flange 26 positioned at the end of shell 14 about aperture 15 in a sealing manner.

The lower end of tubular member 20 rests in an annular ledge 28 of a plate 30, which defines perforations or slots 32 to permit the flow of blood out of the bottom of tubular member 20. Also, this eliminates the possibility of forming an air pocket at the bottom of tube 20 when the blood level rises in reservoir 10. Plate 30 is retained by a silicone rubber end plug 34, defining an aperture which surrounds protrusion 36. Protrusion 36 is part of inwardly upstanding hump 38, which is defined at the bottom end of shell 16.

Tubular member 20 carries, preferably about its exterior, a tubular nylon filter screen 35, which may have a mesh size of about 120 microns for filtration of the blood and the retention of debris. Optional outer tubular sock filter 37 may be a knitted nylon cover layer.

Filter screen 35 and filter 37 are folded at their upper ends about the upper end of tubular member 20, inside of slot 39 of the silicone rubber gasket 24, for frictional retention of the ends of the tubular filters 35, 37. At the lower end, filters 35, 37 pass under slots 32, and then fit through the central aperture of plate 30, between the plate and plug 34, for frictional retention.

Figure 2:
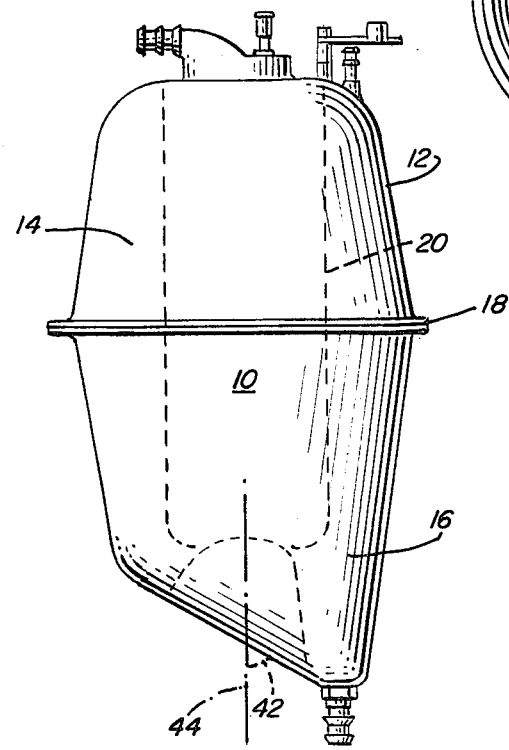
FIG. 2 is an elevational view of the same reservoir.

Annular trough 40 is defined about hump 38 in shell 16, and is angularly positioned to define an acute angle 42 (FIG. 2) to the axis 44 of tubular member 20.

Outlet aperture 46 communicates through the lowest portion of trough 40, so that all blood will easily drain from the reservoir.

As an added advantage of the above described arrangement of the lower end of reservoir 10, the reduced volume of the extreme low end 48 of the reservoir provides improved calibration of low blood volumes in the reservoir. Accordingly, calibration strip 50, having volume indication markings, may be provided along a face of the reservoir so that, at a minimum blood level, blood volumes as small as 25 or 50 cc. can be measured.

At the upper end of reservoir 10 several inlet members are defined. Aperture 52 defines a sleeve member 54 passing through casing 12 in which is fitted luer-lock connector 56 for the addition of supplemental medication when desired. The connector 56 may be of conventional design.

Vent tube 58 is provided with a closable rubber vent cap 60. If desired, a porous hydrophobic material may be placed in vent tube 58, to filter out any contamination while permitting the flow of gas into and out of the reservoir.

Port tube 59 may be used as a connection to a vacuum pump, if desired, being adapted with conventional gripping rings to receive and hold a flexible vacuum line. Also, port tube 59 may be used to prime the reservoir.

Positioned within sleeve 26 is a molded inlet assembly 62. Apertures are defined in inlet assembly 62 in which are positioned a pair of luer-lock connectors 64 similar in design, if desired, to connector 56. The connectors are heat or solvent sealed as desired to the inlet assembly 62. These may be used for adding blood, medicaments, or the like.

Also, inlet assembly 62 defines the three inlet aperture tubes 66 which extend horizontally, i.e., normally to the longitudinal axis of perforated tubular member 20. Tubular apertures 66 terminate inwardly in downwardly curved end walls 68, having open bottoms, so that the blood or other fluid which is directed inwardly through apertures 66 is gently directed downwardly by the curvature of walls 68, passing through sleeve 26 into the defoaming means 23.

Side walls 70 project downwardly from the curved end walls 68 to channel the blood flow, so that interconnecting flow from one tubular aperture 66 to another is substantially prevented. Also, the gentle, curved downward direction of blood greatly reduces spattering through luer apertures 64 when they are open.

Tubular apertures 66 can be seen from FIG. 1 to be positioned radially about the axis 44 of tubular member 20. This provides adequate space for manual access to the tube 66, while at the same time directing all of the flow through them centrally into the reservoir. It can be seen that the extent of the tubes 66 defines an arc of essentially 90°.

The cardiotomy reservoir of this invention thus provides smooth, non-hemolytic inlet of blood without spattering or flow out of other upper apertures. The blood flows downwardly through a relatively large amount of defoaming sponge 23 for gentle and thorough removal of foam and then passes outwardly through slots 32 or apertures 22, depending upon the amount of blood in the reservoir, the flow rate and the like. Complete emptying of the reservoir is provided by the configuration of the bottom of the structure.

Also, tubular member 20 provides internal reinforcement of the casing 12 in the case where a reduced pressure is used inside of the reservoir.

The above has been offered for illustrative purposes only and is not intended to limit the invention of this application, which is as defined in the claims below.

That which is claimed is:

1. A blood reservoir which comprises: a rigid casing, a perforated tubular member positioned within said casing and extending between the ends thereof; inlet aperture means positioned at the upper end of said reservoir in communication with the bore of said tubular member to provide fluid communication from the exterior to said bore; flow aperture means positioned at the lower end of said tubular member to provide fluid communication between said bore and the casing interior, said bore containing blood defoaming means, and said tubular member carrying blood filter means to filter flow through the perforations of the tubular member and the flow aperture means, said inlet aperture means defining a plurality of tubular apertures having open ends which are outwardly directed normally of the longitudinal axis of the tubular member, said apertures inwardly terminating in open-bottom, downwardly curved end wall means to direct fluid flow inwardly through said apertures and then downwardly by means of a gentle, curved flow into said defoaming means, and outlet aperture means positioned adjacent the bottom of said casing in exterior relation to said tubular member.

2. The blood reservoir of claim 1 in which side walls project downwardly from said downwardly curved end wall means to prevent interconnecting flow from one tubular aperture to another.

3. The blood reservoir of claim 1 in which said tubular apertures are each positioned radially of the axis of said tubular member.

4. The blood reservoir of claim 3 in which the bottom of said casing defines an upstanding central hump surrounded by an annular trough, the plane of the bottom of said annular trough defining an acute angle to the axis of said tubular member, said outlet aperture communicating through the lowest portion of said trough, and a perforated plate member carried on said hump, said plate member carrying the lower end of said tubular member.

5. The blood reservoir of claim 4 in which said radially positioned tubular apertures are all positioned in no more than an arc of 120°.

6. In a blood reservoir which comprises a rigid casing having inlet and outlet means for blood, having blood filter and defoaming means within, the improved inlet means which comprises a plurality of tubular apertures positioned adjacent to the upper end of said reservoir, said tubular apertures having open ends which are outwardly directed normally of the longitudinal axis of said reservoir, said apertures inwardly terminating in open-bottom, downwardly-curved end wall means, to direct fluid flow inwardly through said aperture and then downwardly by means of a gentle, curved flow in said reservoir, said tubular apertures being each positioned radially of the axis of said reservoir, and side wall means projecting downwardly from said downwardly-curved end wall means, to prevent interconnecting flow from one tubular aperture to another.

7. The blood reservoir of claim 6 in which said radially positioned tubular apertures are all positioned in no more than an arc of 120°.

* * * * *